US009823184B1

(12) United States Patent
Challener et al.

(10) Patent No.: US 9,823,184 B1
(45) Date of Patent: Nov. 21, 2017

(54) DISTRIBUTED GAS DETECTION SYSTEM AND METHOD

(71) Applicant: General Electric Company, Schenectady, NY (US)

(72) Inventors: William Albert Challener, Glenville, NY (US); Sabarni Palit, Niskayuna, NY (US); Jason Harris Karp, Niskayuna, NY (US); Ansas Matthias Kasten, Niskayuna, NY (US); Niloy Choudhury, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 15/154,509

(22) Filed: May 13, 2016

(51) Int. Cl.
 G01N 21/00 (2006.01)
 G01N 21/31 (2006.01)
 G02B 6/02 (2006.01)
 G01N 21/25 (2006.01)

(52) U.S. Cl.
 CPC ....... *G01N 21/3103* (2013.01); *G01N 21/255* (2013.01); *G02B 6/02* (2013.01); *G02B 6/02304* (2013.01); *G01N 2201/0826* (2013.01)

(58) Field of Classification Search
 CPC .............. G01N 21/3504; G01N 21/39; G01N 2021/399; G01N 2201/08; G01N 21/35; G01N 2201/06113; G01N 2201/068; G01N 2021/0346; G01N 21/031; G01N 21/3577; G01N 1/405; G01N 2021/0378; G01N 2021/1793
 See application file for complete search history.

(56) References Cited

U.S. PATENT DOCUMENTS

| 3,977,233 A | 8/1976 | Issel |
| 4,735,095 A | 4/1988 | Issel |
| 5,271,901 A | 12/1993 | Issel et al. |
| 5,992,217 A | 11/1999 | Jax et al. |

(Continued)

FOREIGN PATENT DOCUMENTS

| CN | 105387351 A | 3/2016 |
| EP | 175219 B1 | 3/1986 |

(Continued)

OTHER PUBLICATIONS

Lee, Jung-Ryul et al., "Fiber optic liquid leak detection technique with an ultrasonic actuator and a fiber Bragg grating". Dec. 15, 2005 / vol. 30, No. 24 / Optics Letters, pp. 3293-3295.

(Continued)

*Primary Examiner* — Michael P Stafira
(74) *Attorney, Agent, or Firm* — Nitin N. Joshi (57) ABSTRACT

A distributed gas detection system includes one or more hollow core fibers disposed in different locations, one or more solid core fibers optically coupled with the one or more hollow core fibers and configured to receive light of one or more wavelengths from a light source, and an interrogator device configured to receive at least some of the light propagating through the one or more solid core fibers and the one or more hollow core fibers. The interrogator device is configured to identify a location of a presence of a gas-of-interest by examining absorption of at least one of the wavelengths of the light at least one of the hollow core fibers.

20 Claims, 5 Drawing Sheets

(56) References Cited

U.S. PATENT DOCUMENTS

| | | |
|---|---|---|
| 6,088,417 A | 7/2000 | Jax et al. |
| 6,279,384 B1 | 8/2001 | Heikkinen et al. |
| 6,289,143 B1 | 9/2001 | Berthold et al. |
| 6,796,167 B2 | 9/2004 | Tigerholm |
| 6,898,962 B2 | 5/2005 | Jax |
| 7,011,102 B2 | 3/2006 | Folkers |
| 7,270,019 B2 | 9/2007 | Issel |
| 7,500,489 B2 | 3/2009 | Folkers |
| 7,727,765 B2 | 6/2010 | Organiscak et al. |
| 7,770,435 B2 | 8/2010 | Issel et al. |
| 7,802,465 B2 | 9/2010 | Issel |
| 8,064,738 B2 | 11/2011 | Zandiyeh et al. |
| 8,315,486 B2 | 11/2012 | Pearce et al. |
| 8,520,195 B2 | 8/2013 | Ramos et al. |
| 8,937,280 B2 | 1/2015 | Legrand et al. |
| 2003/0030786 A1* | 2/2003 | Shurgalin ............... G01M 11/31 356/73.1 |
| 2007/0119238 A1 | 5/2007 | Issel |
| 2007/0157744 A1 | 7/2007 | Issel |
| 2008/0053198 A1 | 3/2008 | Issel et al. |
| 2010/0002983 A1 | 1/2010 | Kopp et al. |
| 2012/0105827 A1* | 5/2012 | Carter ................ G01N 21/3504 356/51 |
| 2013/0162979 A1* | 6/2013 | Chen .................. G01N 21/3504 356/51 |
| 2016/0202186 A1* | 7/2016 | Romanak ................ G01J 3/44 356/73 |
| 2017/0097464 A1 | 4/2017 | Challener et al. |

FOREIGN PATENT DOCUMENTS

| | | |
|---|---|---|
| EP | 525593 B1 | 2/1993 |
| EP | 1812777 B1 | 8/2007 |
| EP | 1784602 B1 | 10/2008 |
| WO | 2006089629 A1 | 8/2006 |
| WO | 2006122696 A1 | 11/2006 |

OTHER PUBLICATIONS

Martin, "New Vapor Method Detects and Locates Leaks From Pipelines", Leak Detection for Underground Storage Tanks, American Society for Testing and Material, pp. 123-130, Jan. 1993.

Spirin et al., "Fiber Optic Bragg Grating-Based Sensor for Liquid Hydrocarbon Leak Detection and Localization", Smart Structures and Materials: Sensory Phenomena and Measurement Instrumentation for Smart Structures and Materials, vol. No. 3986, pp. 292-299, 2000.

Geiger et al., "Leak Detection and Locating — a Survey", Pipeline Simulation Interest Group, pp. 1-20, Oct. 15-17, 2003.

Guan et al., "Bragg Gratings in Pure-Silica Polarization-Maintaining Photonic Crystal Fiber", IEEE Photonics Technology Letters, vol. No. 20, Issue No. 23, pp. 1980-1982, Dec. 1, 2008.

Shaw et al., "Leak Detection Study-DTPH56-11-D-000001", U.S. Department of Transportation Pipeline and Hazardous Materials Safety Administration, pp. 0339-1201, Dec. 10, 2012.

Yang et al., "A Two Fiber Bragg Grating Gas Leakage Detection Sensor", Photonics Global Conference (PGC), pp. 1-6, Dec. 13-16, 2012.

* cited by examiner

DISTRIBUTED GAS DETECTION SYSTEM AND METHOD

GOVERNMENT LICENSE RIGHTS

This invention was made with Government support under contract number DE-AR0000543 awarded by the Department Of Energy. The Government has certain rights in this invention.

BACKGROUND

Various devices have been developed for sensing and measuring the concentrations of different gases at man-made or natural locations, such as oil wells, pipelines, mines, manufacturing plants, refineries, and the like. Monitoring for the presence and concentration of gases may be used for various applications, such as to ensure that toxic gases (CO, $H_2S$, etc.) are not present in significant concentrations, to ensure that explosive gases ($CH_4$, $H_2$, etc.) are below respective explosive limits, to identify the gases in a mixture (for custody transfer, heat content, etc.), or for various other reasons. Spectroscopy may be used to provide highly sensitive and selective sensors because each gas exhibits a unique spectroscopic fingerprint, such that gases absorb and emit light energy at specific wavelengths. Gases are relatively transparent, however, so the absorption line strength of a gas may be relatively small and hard to detect.

To accommodate for the small absorption line strength, light used in spectroscopy is required to pass through long path lengths in the gas in order to establish sufficient sensitivity for a spectroscopic sensor to provide a measurement of a concentration of a gas of interest in a test sample, for example. For example, a light source of the spectroscopic sensor may be separated from a detector of the spectroscopic sensor by a distance of one kilometer or more to achieve a necessary path length, but such distances are not practical in most applications.

Other known types of spectroscopic sensors define an optical cavity with two mirrors and are referred to as optical cavity sensors. The gas is contained within the optical cavity, and the light is reflected between the two mirrors multiple times before being detected. While this technique allows for a manageable device size, it is problematic due to the need to maintain very exacting alignment of the mirrors. Variations in conditions, such as temperature changes, vibration, humidity, or the like, may misalign the mirrors or otherwise interfere with the sensitivity and/or accuracy of these optical cavity sensors. Therefore, this technique is generally not used for remote, unattended measurements in various field environments, such as an oil or gas well pad, a pipeline, a mine, or the like. Moreover, optical cavity sensors are generally quite expensive.

Some gas leak detection systems use a sensing pipe or tube located near a pipeline through which the gas is conveyed. This sensing pipe or tube may have openings to allow gas leaking from the pipeline to diffuse into the sensing pipe or tube. A burst of air or another gas may be introduced into the sensing pipe or tube to move the gas leaking from the pipeline through the sensing pipe or tube. The sensing pipe or tube may include a gas sensor at one end to sense the leaking gas that is pushed through the sensing pipe or tube by the air burst toward the sensor.

These types of leak detection systems may be unable to accurately determine the location of the leak along the length of a very long pipeline. The location of the leak is approximated based on the concentration of the gas detected at the sensor and the time delay between when the air burst is introduced into the sensing pipe or tube. Because the gas may disperse along the length of the sensing pipe or tube by the air burst, it can be difficult or impossible to accurately determine where the gas first diffused into the sensing pipe or tube if the gas must travel through the tube for a very long distance before reaching the sensor at the end of the tube.

BRIEF DESCRIPTION

In one embodiment, a distributed gas detection system includes one or more hollow core fibers disposed in different locations, one or more solid core fibers optically coupled with the one or more hollow core fibers and configured to receive light of one or more wavelengths from a light source, and an interrogator device configured to receive at least some of the light propagating through the one or more solid core fibers and the one or more hollow core fibers. The interrogator device is configured to identify a location of a presence of a gas-of-interest by examining absorption of at least one of the wavelengths of the light at least one of the hollow core fibers.

In one embodiment, a distributed gas sensing system includes one or more hollow core fibers disposed in different locations, one or more solid core fibers optically coupled with the one or more hollow core fibers and configured to receive light of one or more wavelengths from a light source, and an elongated sensing tube having openings through which a gas-of-interest may enter into the sensing tube from a source of the gas-of-interest. The one or more hollow core fibers are at least partially disposed inside the sensing tube. The system also includes an interrogator device configured to receive at least some of the light propagating through one or more of the solid core fibers and one or more of the hollow core fibers. The interrogator device is configured to identify a location of a presence of the gas-of-interest from the source by examining absorption of at least one of the wavelengths of the light at one or more of the hollow core fibers.

In one embodiment, a method includes receiving light that has propagated through one or more solid core fibers and one or more hollow core fibers of several hollow core fibers disposed in different locations, determining whether one or more wavelengths of the light have been at least partially absorbed by a gas-of-interest inside one or more of the hollow core fibers based on the light that is received, and determining a location of a source of the gas-of-interest based on a location of the one or more hollow core fibers in which the one or more wavelengths of the light was at least partially absorbed by the gas-of-interest.

DETAILED DESCRIPTION

Various embodiments will be better understood when read in conjunction with the appended drawings. To the extent that the figures illustrate diagrams of the functional blocks of various embodiments, the functional blocks are not necessarily indicative of the division between hardware (including circuitry). Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings. The sizes of the components shown in the drawings may not be to scale and/or may have different aspect ratios.

As used herein, the terms "system," "unit," or "device" may include a hardware and/or software system that operates to perform one or more functions. For example, a device, unit, or system may include one or more computer processors, microprocessors, field programmable gate arrays, integrated circuits, controllers, or other logic-based devices that perform operations based on instructions stored on a tangible and non-transitory computer readable storage medium, such as a computer memory. Alternatively, a device, unit, or system may include a hard-wired device that performs operations based on hard-wired logic of the device. The device or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

One or more embodiments of the inventive subject matter described herein provide distributed gas leak detection systems and methods. The systems and methods can detect the presence of a gas leaking out of a pipeline and a location of the leak. For example, methane can leak from oil and gas well pads or from pipelines. Methane also is a troublesome source of explosions in underground coal mines. Due to the large areas over which the gas may be present, multiple sensing locations may be needed to determine a location of the source of the leak.

The systems and methods described herein may use hollow core optical fibers (HCF) for transporting infrared light (or other wavelengths of light) along relatively long path lengths to sensitively detect methane and other types of gas leaks. The HCF is penetrated with holes from the side at different locations along the length of the HCF so that leaking gases in the external environment can diffuse into the hollow core of the HCF where the light beam is propagating. Optical absorption measurements such as tunable diode laser absorption spectroscopy (TDLAS) can be used to make highly sensitive measurements of the gas concentration and also to distinguish between different types of gases which exhibit different absorption wavelengths based on the light that is received through the HCF.

The systems and methods described herein may be used to detect and measure concentrations of gases of interest in various applications. For example, the gas sensing system may be used to monitor gases at oil wells or well pads, along pipelines, in mines, in manufacturing plants, at refineries, in factories, and the like. One particular application is measurement of fugitive methane emissions from oil and gas well pads. Methane is a strong contributor to the greenhouse effect, which traps infrared radiation within the earth's ozone layer. The low cost, but highly sensitive (~10 parts per million, or ppm) gas sensing systems described herein may be disposed at oil and gas well pads to monitor methane emissions. The monitoring of methane emissions may be in order to comply with regulations designed to reduce greenhouse gas emissions, to reduce loss of methane that could be sold as product, or the like. Although the gas sensing system is located in the field at the oil and gas well pad, the gas sensing system may be monitored remotely, allowing for remote monitoring of multiple gas sensing systems at different oil and gas well pads, for example.

Spectroscopy can be used for gas sensing by detecting the wavelengths that gas samples absorb and emit light energy. These wavelengths, referred to as absorption spectra, are specific or unique to the types of gases. For example, methane has several absorption bands at different wavelengths, such as an absorption band at 1.65 microns in the near infrared (NIR) range. This absorption band lies within the "window" of wavelengths used by the telecom industry to transport data through conventional solid core optical fiber, which extends from 1260 nm ("O" band) up to 1675 nm ("U/XL" band). Other gases with absorption lines in this wavelength range include water, $CO_2$, $H_2S$, and ammonia.

Microstructured (or "holey") optical fibers have fiber structures that are porous and make use of this porosity in several different ways to confine light to the core of the fiber so that it can propagate for long distances along the fiber. These types of fibers may be used as the HCF described herein. U.S. patent application Ser. No. 14/876,411 describes various hollow core microstructured fibers that may be used as the HCF described herein, and the entire disclosure of this application is incorporated herein by reference.

Figure 1:
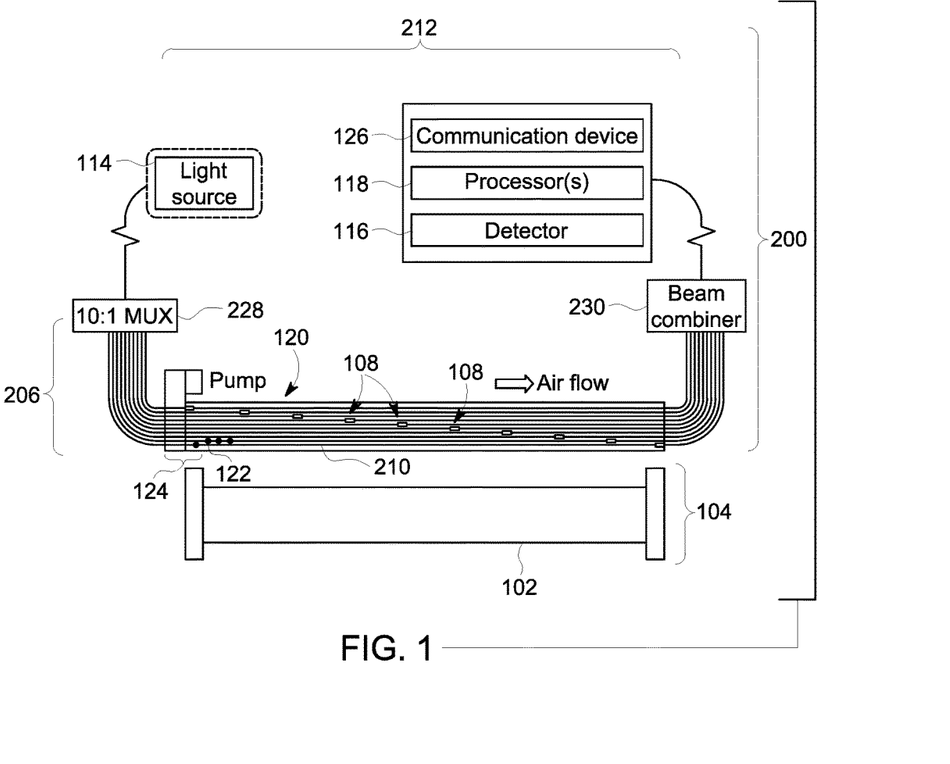
FIG. 1 illustrates an embodiment of a distributed gas leak detection system.

FIG. 1 illustrates one embodiment of a distributed gas leak detection system 200. The system 200 detects the presence, concentration, and/or location of one or more gases of interest along a remote test location 104. In the illustrated embodiment, the remote test location 104 is a pipeline carrying the one or more gases of interest, but optionally, the remote test location 104 may be an underground mine, a landfill, a water treatment plant, a platform of an oil or gas well, etc. The system 200 monitors for the gases of interest along a length of the test location 104. The test location 104 may be subject to environmental conditions that may be damaging to certain electronic equipment, such as thermocouples, LEDs or photodiodes, or may contain explosive mixtures of gases or other substances for which it is not possible to proximately locate electrical equipment. For example, the test location 104 may be a geothermal well, oil and/or gas well, oil and/or gas well pad, oil and/or gas pipeline, a mine, or the like. The test location 104 in other examples may be an industrial facility, such as a manufacturing plant, a refinery, or a factory. As one more example, the test location 104 may be a wellbore used in conjunction with hydraulic fracturing.

The test location 104 may be understood as being remote in that the test location 104 is located at a distance from components of the system 200 configured to generate and/or receive signals conveyed through the test location 104. For example, parts of a pipeline 102 that is included in or represents the test location 104 may be 100 kilometers away from components of the system 200. Thus, signal generation and/or signal processing equipment, for example, may be maintained under different environmental conditions than the components of the system 200 along the remote test location 104. Alternatively, signal generation and/or signal processing components of the system 200 may be located at the remote test location 104, and may be housed within protective cases or housings to protect such components from the environmental conditions of the test location 104, such as hot and cold temperatures, moisture, debris, vibration, explosive gas mixtures, and the like.

The system 200 includes an optical fiber assembly 206 that extends along various lengths or the entire length of the test location 104. The optical fiber assembly 206 may be formed from plural HCFs 108 optically coupled with solid core optical fibers 210. In contrast to the HCFs 108, the solid core optical fibers 210 may be optical fibers that do not have a hollow interior. The HCFs 108 and solid core fibers 210 may be optically coupled with each other when light can be transmitted along and within the HCFs 108 and solid core fibers 210.

In the illustrated embodiment, the optical fiber assembly 206 extends through a perforated sensing tube 120 that extends along the test location 104. The sensing tube 120 may be a plastic tube or a volume of space in which the fiber assembly 206 is disposed (e.g., between a plastic sheet and the pipeline 102). The sensing tube 120 includes openings 122 through which gas in the test location 104 (e.g., leaking from the pipeline 102) can diffuse into the interior space of the tube 120 and into the HCFs 108. Although only a few openings 122 are shown, many more openings 122 may exist at different locations along the length of the sensing tube 120. The sensing tube may also be covered with a membrane that is permeable to the gases of interest but which resists or impedes in the ingress of water or other liquids and/or gases that are not of interest or which could clog the tube.

The fiber assembly 206 includes several different solid core fibers 210 separately coupled with different HCFs 108. Each HCF 108 may be connected with and disposed between solid core fibers 210 on opposite sides of the HCF 108. The HCFs 108 may be disposed at different locations along the length of the sensing tube 120 to provide for distributed sensing of gas leaks. For example, the lengths of the solid core fibers 210 extending from the light source 114 to the HCFs 108 may be different for different HCFs 108, as shown in FIG. 1. Alternatively, the fiber assembly 206 may include a string of a series of solid core fibers 210 separated from each other by HCFs 108.

The system 200 includes an interrogator device 212 that detects the presence and/or location of one or more gases of interest along the length of the fiber assembly 206. The interrogator device 212 includes a light source 114 that is optically coupled with the fiber assembly 206. As used herein, two components are "optically coupled" when there is a sufficient amount of light being emitted from one of the components to be detected at the other component. The light source 114 generates light that is transmitted to the fiber assembly 206. The light source 114 may be a laser that emits light in the infrared range, such as the near-IR range. The light generated by the light source 114 enters into and propagates through the solid core fibers 210 to the HCFs 108. The hollow cores of the HCFs 108 receive the light from the solid core fibers 110.

The HCFs 108 may include port holes that extend from an exterior surface of the HCFs 108 into the hollow cores of the HCFs 108. The port holes are sized to allow for gas in the external environment (e.g., which may be leaking from the pipeline 102 or another source) to diffuse into the hollow core, where the gas can interact with the light propagating through the core. As used herein, "interaction" of a gas with the light involves the absorption and emission of light energy by the gas at various wavelengths, which affects and/or alters the characteristics of the light energy propagating through the hollow core of the fiber.

In the illustrated embodiment, the light source 114 emits the light into one or more solid core fibers to a multiplexer 228 ("10:1 MUX" in FIG. 1), which divides the light and conveys the divided light into the solid core fibers 210 that are optically coupled with different HCFs 108. The multiplexer 228 may convey the light received from the light source 114 into different solid core fibers 210 at different times. The light propagating through the core of the HCFs 108 continues to propagate through the solid core fibers 210 on the other sides of the HCFs 108 to a beam combiner 230. The beam combiner 230 receives the light from the different solid core fibers 210 before conveying the received light to the detector 116.

A detector 116 measures the received light. The detector 116 may be an optical sensor, an optical camera, or the like, configured for use in infrared gas-phase spectroscopy. One or more processors 118 of the interrogator device 212 represent hardware circuitry that includes and/or is connected with one or more microprocessors, field programmable gate arrays, or integrated circuits. The processors 118 determine a presence, concentration, and/or location of one or more gases in the HCFs 108 based on the light received by the detector 116. For example, the processors 118 can analyze the reflected light to identify various gases of interest within the HCFs 108 that interacted with the light to detect the presence of such gases. The processors 118 may analyze the light using gas-phase IR spectroscopy. For example, the processors 118 may compare the detected wavelengths of absorption bands in a test sample to known absorption band wavelengths of known gases in order to identify one or more gases in the test sample. In addition to identifying the gases, the processors 118 may also determine the concentrations of the gases. The processors 118 may determine that the gas in the HCFs 108 includes water vapor, carbon dioxide, methane, and ethane, for example, and may also detect the concentrations and/or relative concentrations of these identified gases.

The processors 118 may be configured to generate a control signal in response to detecting a leak, such as to send an alert. The processors 118 may also generate other control signals responsive to detecting one or more gases of interest, such as for automatically scheduling additional inspection, to initiate a shutdown of the well, to activate a system that stops gas leaking or egress, or the like. For example, the interrogator device 212 may include a communication device 126 that communicates a signal to another location, such as a signal that notifies others of a detected leak and/or the location of the leak, a signal that causes one or more valves to close and stop the gas conveyed through the pipeline 102 from being pumped through the pipeline 102, etc. The communication device 126 can represent one or more antennas, modems, and/or associated transceiving circuitry.

In one embodiment, the solid core fibers 210 and HCFs 108 convey the light generated by the light source 114 in a variety of modes, and are not limited to propagating the light along the fibers 210 and HCFs 108 in only one mode. Light may propagate through optical fibers such as the solid core fibers 210 in a vertical polarization mode, a horizontal polarization mode, and/or a combination or mixture of vertical and horizontal polarizations of the light. The fibers 210 and HCF 108 may not be limited to propagating or conveying only a single mode of light. For example, the light propagating through the solid core fibers 210 and the HCFs 108 may propagate through the solid core fibers 210 to the HCFs 108 (and optionally through one or more the HCFs 108 before reaching one or more other HCFs 108) in a vertical polarization, horizontal polarization, and/or a mixture of vertical and horizontal polarizations. The light may continue or be reflected back to the detector 116 in the same or different polarization. For example, the fibers 108, 210 may not restrict propagation of light either to or from an HCF 108 to a single polarization or mode.

In one embodiment, the system 200 includes a control gas source 124 (e.g., "pump" in FIG. 1) that provides a burst of gas or air into the sensing tube 120. The gas or air provided by the source 124 may be different from the gas of interest being detected by the system 200 to prevent confusion between detection of a leak versus the gas or air provided by the source 124. The source 124 may be a pump or fan that pushes ambient air through the sensing pipe 120. The source 124 may push air or another gas through the sensing pipe 120 on a periodic, irregular, or on-demand basis to move gas leaking in the test location 104 through the sensing pipe 120. The leaking gas will have a greater local concentration in the sensing pipe 120 when compared to other locations. The localized concentration of the leaking gas can be moved through the sensing pipe 120 by the pushed air or gas from the source 124. As the leaking gas moves through the sensing pipe 120, the interrogator device 212 can emit light and measure reflected light to identify locations in which the leaking gas concentration is located, as well as track movement in the sensing tube 120, to assist in identifying where the leak is located along or in the test location 104.

As described above, the remote test location 104 may represent an area or volume around or along a pipeline carrying the one or more gases of interest, but optionally may be around, along, or within an underground mine, a platform of an oil or gas well, etc. The systems described herein may include the HCFs 108 in different locations within an area sought to be monitored for the presence of one or more gases of interest, such as but not limited to methane. The HCFs 108 may be positioned at different locations along the length of a pipeline, in different locations of an underground mine, in different locations on a mining platform, or the like, to detect the presence of a gas. While the descriptions and illustrations shown herein relate to HCFs 108 disposed along the length of a pipeline, not all embodiments of the inventive subject matter are limited to pipelines.

In contrast to using a single HCF 108 to detect the presence and/or location of a gas leak along the test location 104, the system 200 may include several HCFs 108 in different locations along the test location 104 to detect the presence and/or location of the gas leak. The HCFs 108 may be spaced apart from each other by relatively large distances, such as ten kilometers or another distance, to provide for leak detection along the test location 104 that extends over a very large area or distance. The solid core fibers 210 may allow for propagation of light through the fibers 210 over larger distances than the HCFs 108. As a result, the solid core fibers 210 may be spliced with the HCFs 108 to allow for the HCFs 108 to be spaced far apart from the light source 114 and/or the detector 116.

Additionally, the solid core fiber or fibers 210 that connect the fiber assembly 206 with the interrogator device 212 can allow for the interrogator device 212 to be located relatively far from the test location 104. The interrogator device 212 may be placed far from the test location 104 such that the risk for explosion from leaking gas in the location of the interrogator device 212 may be very low or nonexistent. This can permit the interrogator device 212 to operate without having reduced power restrictions and/or without being located within explosion-proof packaging relative to interrogator devices that are close to the test location 104.

Figure 2:
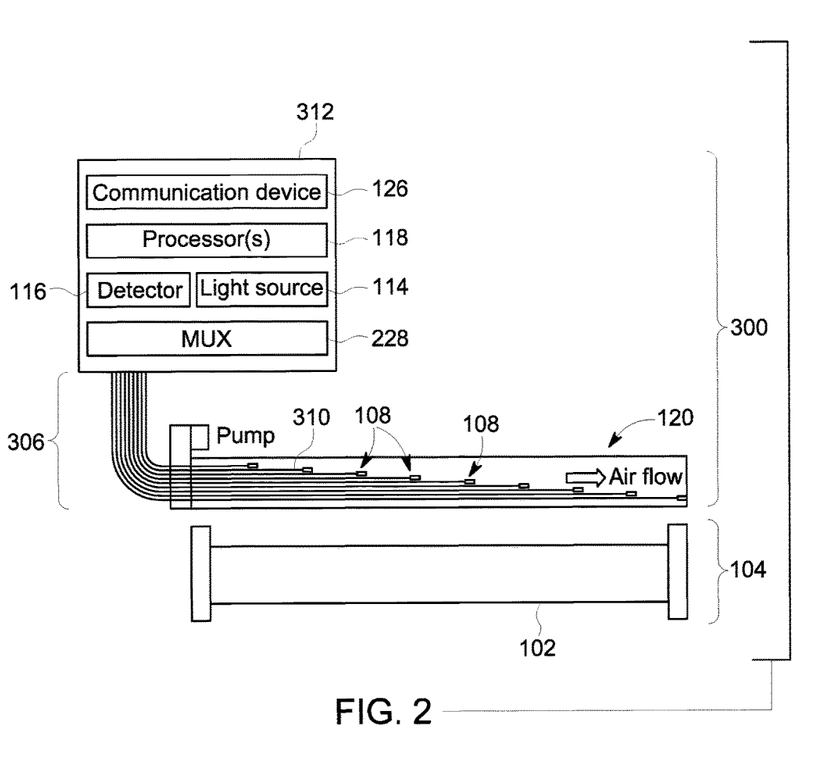
FIG. 2 illustrates another embodiment of a distributed gas leak detection system.

FIG. 2 illustrates another embodiment of a distributed gas leak detection system 300. Similar to the system 200 shown in FIG. 1, the system 300 detects the presence, concentration, and/or location of one or more gases of interest along the test location 104. The system 300 includes an optical fiber assembly 306 that extends along various lengths or the entire length of the test location 104. The optical fiber assembly 306 may be formed from plural HCFs 108 optically coupled with solid core optical fibers 310. In contrast to the HCFs 108, the solid core optical fibers 310 may be optical fibers that do not have a hollow interior. The HCFs 108 and solid core fibers 310 may be optically coupled with each other when light can be transmitted along and within the HCFs 108 and solid core fibers 310. The fiber assembly 306 may be at least partially disposed within the sensing tube 120. Although the openings 122 (shown in FIG. 1) in the sensing tube 120 are not visible in FIG. 2, the sensing tube 120 may include the openings 122 to permit gas outside of the sensing tube 120 to reach the HCFs 108. The sensing tube may also be covered with a membrane that is permeable to the gases of interest but which resists or impedes in the ingress of water or other liquids and/or gases that are not of interest or which could clog the tube.

In contrast to the fiber assembly 206 shown in FIG. 1, the fiber assembly 306 includes several different solid core fibers 310 separately coupled with different HCFs 108. Each HCF 108 may be connected with one solid core fiber 310 on one side of the HCF 108. The solid core fibers 310 have different lengths such that the HCFs 108 are disposed at different locations along the length of the sensing tube 120 to provide for distributed sensing of gas leaks. The HCFs 108 can include reflectors inside, at, or near the ends of the HCFs 108 that are opposite the ends that connect with the solid core fibers 310 to reflect light.

The system 300 includes an interrogator device 312 that detects the presence and/or location of one or more gases of interest along the length of the fiber assembly 306. The interrogator device 312 includes the light source 114 that is optically coupled with the fiber assembly 306 on one end of the fiber assembly 306. The light source 114 generates light that is transmitted to the fiber assembly 306. In the illustrated embodiment, the light source 114 emits the light into one or more solid core fibers to the multiplexer 228 ("MUX" in FIG. 2), which divides the light and conveys the divided light into the solid core fibers 310 that are optically coupled with different HCFs 108. The light propagating through the core of the HCFs 108 is reflected back to the detector 116 of the interrogator device 312.

The multiplexer 230 receives the reflected light from the different solid core fibers 310 before conveying the received light to the detector 116. As described above, the detector 116 receives the light and the processors 118 examine the light to determine the presence and/or location of a gas leak along or within the test location 104.

Figure 3:
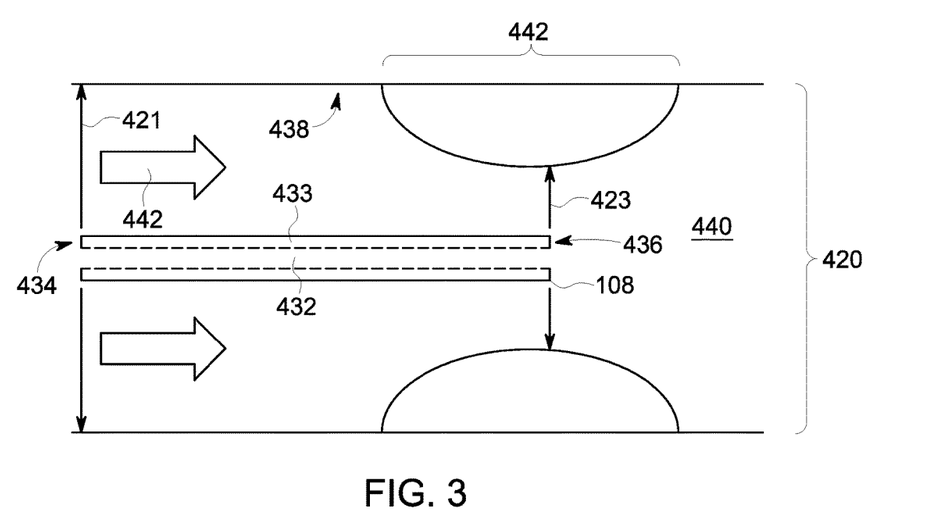
FIG. 3 illustrates a cross-sectional view of a segment of a sensing tube and a hollow core fiber that may be disposed inside the sensing tube according to one embodiment.

FIG. 3 illustrates a cross-sectional view of a segment of a sensing tube 420 and one of the HCFs 108 that may be disposed inside the sensing tube 420 according to one embodiment. The sensing tube 420 may represent one or more of the sensing tubes described herein. As shown in FIG. 3, the HCF 108 may have a hollow core 432 radially surrounded or encompassed by a cladding 433, as described in U.S. patent application Ser. No. 14/876,411. Not shown in FIG. 3 are the solid core fibers 210, 310 (shown in FIGS. 1 and 2) that may be optically coupled with the HCF 108, as described above.

In order to measure the presence of gas leaking from the source 102 (shown in FIG. 2), the gas typically enters the sensing tube 420 through one or more openings 122 (not shown in FIG. 3 but shown in FIG. 1) and gradually moves into the hollow core 432 of the HCF 108. Movement of the gas into the hollow core 432 may take a considerable amount of time, such as several hours or days, due to the relatively low concentration of gas that may leak from the source 102 and the corresponding rate of diffusion. As a result, a gas leak detection system using the HCFs 108 to detect the leaking gas may not have sufficient gas inside the hollow core 432 of one or more HCFs 108 to detect the leak for a considerable amount of time following commencement of the leak.

The sensing tube 420 includes an interior shape that increases the rate at which gas leaking from the source 102 may enter into the hollow cores 432 of one or more of the HCFs 108 inside the sensing tube 420. This can result in more gas entering into the HCF(s) 108 sooner after a leak begins relative to other sensing tubes. The sensing tube 420 generates a pressure differential across opposite ends 434, 436 of the HCF 108 that causes the gas to be drawn into the hollow core 432 of the HCF 108.

The sensing tube 420 includes an interior surface 438 that radially extends around or encompasses an interior space 440 of the tube 420. The openings 122 that permit leaking gas to enter into the tube 420 extend through an outer body 442 of the tube 420 to provide access to the interior space 440 of the tube 420. Consequently, the gas leaking from the source 102 can enter into the interior space 440 of the tube 420. The interior surface 438 may have a reduced throat 442 at or closer to one end 436 of the HCF 108 than the opposite end 434 of the same HCF 108. The reduced throat 442 is a section of the tube 420 where the cross-sectional area of the interior space 440 of the tube 420 is smaller than in a location at or closer to the opposite end 434 of the HCF 108. For example, a cross-sectional area 421 of the tube 420 (measured in a plane that is perpendicular to the flow direction 442 and/or a center axis of the tube 420) that is at the end 434 of the HCF 108 may be larger than a cross-sectional area 423 of the tube 420 (measured in a plane that is perpendicular to the flow direction 442 and/or a center axis of the tube 420) that is at the end 436 of the HCF 108. The smaller area 423 restricts the flow of gas and air through the tube 420 relative to the larger area 421.

The difference in cross-sectional areas in the sensing tube 420 at different ends 434, 436 of the HCF 108 causes a pressure differential in the leaking gas between the different ends 434, 436. This pressure differential can cause the gas to be drawn, pulled, or otherwise sucked into the interior core 432 of the HCF 108. For example, the pressure of gas leaking from the source 102 inside the sensing tube 420 may be lower in the volume of the interior space 440 of the tube 420 within the reduced throat 442 of the tube 420 than in other volumes of the interior space 440 of the tube 420. This lower pressure at the end 436 of the HCF 108 may cause the gas to be drawn, pulled, or sucked into the interior core 432 of the HCF 108 through the end 434 of the HCF 108. The end 434 of the HCF 108 in the volume of the sensing tube 420 where the leaking gas pressure is higher than the volume in which the opposite end 436 of the HCF 108 is located can be referred to as the higher pressure end while the opposite end 436 may be referred to as the lower pressure end.

This pressure differential forces the leaking gas into the hollow core 432 of the HCF 108 faster than a smaller pressure differential. The interior shape of the sensing tube 420 can create the pressure differential to cause the concentration of leaking gas inside the hollow core 432 to become larger in shorter time periods than a smaller pressure differential. Greater concentrations or amounts of the gas within an HCF 108 can result in the presence of the gas to be more likely to be detected than smaller concentrations within an HCF 108. As a result, the leaking gas may be detected sooner than in systems without the pressure differential.

While only a single reduced throat section of the sensing tube 420 is shown in FIG. 3, the sensing tube 420 may include several reduced throat sections. For example, several or all of the HCFs 108 may each be located in the sensing tube 420 with one end of the HCF 108 within a respective reduced throat area of the tube 420 and the opposite end of the HCF 108 within a larger area of the tube 420.

Figure 4:
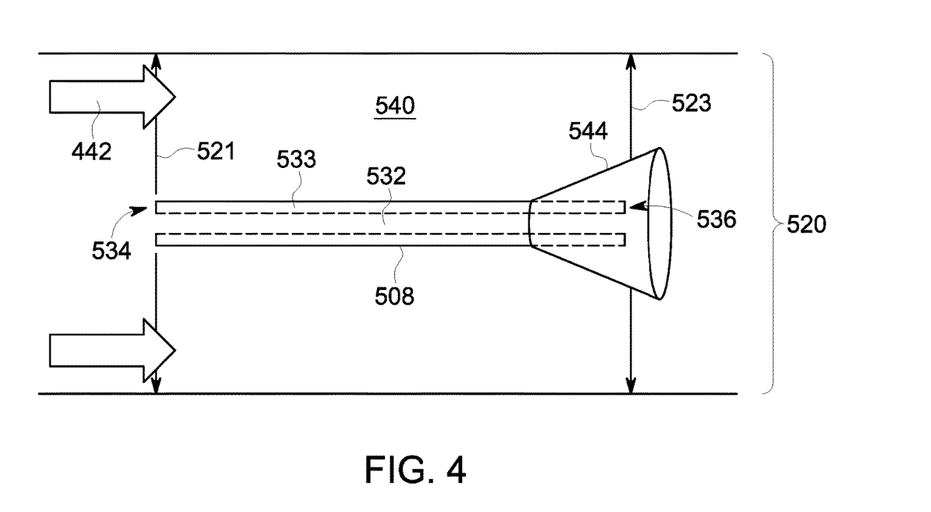
FIG. 4 illustrates a cross-sectional view of a segment of a sensing tube and a hollow core fiber that may be disposed inside the sensing tube according to one embodiment.

FIG. 4 illustrates a cross-sectional view of a segment of a sensing tube 520 and an HCF 508 that may be disposed inside the sensing tube 520 according to one embodiment. The sensing tube 520 may represent one or more of the sensing tubes described herein. The HCF 508 may be similar to the HCF 108 described above. For example, the HCF 508 may have a hollow core 532 radially surrounded or encompassed by a cladding 533 and may allow light to propagate through the interior core 532 to detect the presence of gas, as described in U.S. patent application Ser. No. 14/876,411. Not shown in FIG. 4 are the solid core fibers 110, 210, 310 (shown in FIGS. 1 through 2) that may be optically coupled with the HCF 508, as described above.

Also as described above, in order to measure the presence of gas leaking from the source 102 (shown in FIG. 1), the gas typically enters the sensing tube 520 through one or more openings 122 (not shown in FIG. 4 but shown in FIG. 1) and gradually moves into the hollow core 532 of one or more of the HCFs 508. In order to increase the rate at which the gas enters into the hollow core 532 of one or more HCFs 508 and reduce the time needed for detecting presence of the gas (also referred to as a detection time), one or more of the HCFs 508 may include a baffle 544. The baffle 544 can generate a pressure differential within the sensing tube 520, similar to the reduced throat 442 of the sensing tube 420 shown in FIG. 3. This pressure differential can draw, pull, or suck the gas in the sensing tube 520 into the HCFs 508.

In the illustrated embodiment, the baffle 544 is a cone-shaped body with the smaller diameter cross-sectional area of the body attached or disposed closer to one end 536 of an HCF 508 than an opposite end 534 of the same HCF 508. Optionally, the baffle 544 may have another shape, such as a pyramidal shape, a frustoconical shape, a spherical shape, or the like, or may be formed from planar bodies extending from the HCF 508. The baffle 544 is oriented at an obtuse angle with respect to the portion of the outer surface of the cladding 533 of the HCF 508 that is outside of the baffle 544 (e.g., upstream of the baffle 544 along the flow direction 442) and at an acute angle with respect to the portion of the outer surface of the cladding 533 of the HCF 508 that is inside the baffle 544 (e.g., downstream of the baffle 544 along the flow direction 442).

The baffle 544 may be disposed closer to the end 536 of one HCF 508 to generate a pressure differential in the gas being sensed between the ends 534, 536 of the HCF 508. Similar to the reduced throat 442 in the tube 420 shown in FIG. 3, the baffle 544 may reduce the cross-sectional area of an interior space 540 of the tube 520 at or near the end 536 of an HCF 508 relative to the other end 534 of the same HCF 508. The gas and/or air flowing in the interior space 540 of the tube 520 (e.g., due to the flow of air along the flow direction 442) has a reduced cross-sectional area 523 in which to flow between the baffle 544 and the interior surface of the tube 520 relative to a cross-sectional area 521 between the HCF 508 and the interior surface of the tube 520 in locations of the tube 520 that are farther from or that do not include the baffle 544. As a result, a pressure differential is generated, with the pressure of the gas in the tube 520 being lower at, near, or closer to the end 536 of the HCF 508 than the opposite end 534 of the same HCF 508.

This pressure differential can cause the gas to be drawn, pulled, or otherwise sucked into the interior core 532 of the HCF 508. For example, the pressure of gas leaking from the source 102 inside the sensing tube 520 may be greater in the volume of the interior space 540 of the tube 520 within the reduced cross-sectional area between the baffle 544 and the interior surface of the tube 520 than in other volumes of the interior space 540 of the tube 520. This lower pressure at the end 536 of the HCF 508 may cause the gas to be drawn, pulled, or sucked into the interior core 532 of the HCF 508 through the end 534 of the HCF 508.

The pressure differential forces the leaking gas into the hollow core 532 of the HCF 508 faster than a smaller pressure differential. Greater concentrations or amounts of the gas within an HCF 508 can result in the presence of the gas to be more likely to be detected than smaller concentrations within an HCF 508. As a result, the leaking gas may be detected sooner than in systems without the pressure differential.

Figure 5:
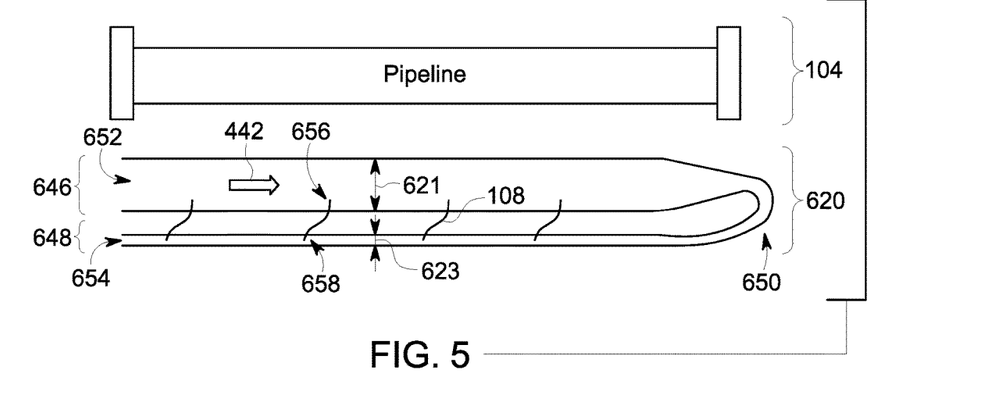
FIG. 5 illustrates a cross-sectional view of a segment of a sensing tube according to one embodiment.

FIG. 5 illustrates a cross-sectional view of a segment of a sensing tube 620 according to one embodiment. The sensing tube 620 may represent one or more of the sensing tubes described herein. The sensing tube 620 includes a larger diameter stage or segment 646 and a smaller diameter stage or segment 648. As shown in FIG. 5, a cross-sectional area 621 through which gas leaking from the source 102 and/or air flows in the larger segment 646 of the sensing tube 620 may be larger than a cross-sectional area 623 through which gas leaking from the source 102 and/or air flows in the smaller segment 648 of the sensing tube 620.

In contrast to the sensing tube 120 shown in FIGS. 1 through 2, the sensing tube 620 may extend from one end 652 to an opposite end 654, with the opposite ends 652, 654 disposed closer together (e.g., at the same end of the test location 104 shown in FIG. 1) than the tube 620 without the bend 650 (e.g., the tube 120 shown in FIG. 1). Placing the ends 652, 654 of the tube 620 closer together can allow for more components of the gas leak detection system to be co-located than if the ends 652, 654 were located farther apart. For example, the pump 124 (shown in FIG. 1) can be coupled with the end 652 and co-located with the interrogator device 212 (shown in FIG. 1), instead of at opposite ends of the sensing tube 120.

The segments 646, 648 are fluidly coupled with each other. In the illustrated embodiment, the segments 646, 648 are fluidly coupled by a bend 650 in the tube 620. Optionally, another conduit may be used to fluidly couple the segments 646, 648. The fluid coupling of the segments 646, 648 allows air flowing from the pump 124 at or coupled with the end 652 of the tube 620 to flow (with gas leaking from the source 102 in the event of a leak) through the larger segment 646 of the tube 620 along the flow direction 442, through the bend 650 or other fluid coupling between the segments 646, 648, and through the smaller segment 648 (e.g., in a direction that is opposite the flow direction 442 in the larger segment 646).

Several HCFs 108 may be coupled with the sensing tube 620. Not shown in FIG. 5 are the solid core fibers 110, 210, 310 (shown in FIGS. 1 through 2) that may be optically coupled with the HCF 108, as described above. In the illustrated embodiment, one end 656 of each of the HCFs 108 extends into the larger segment 646 of the sensing tube 620 (e.g., through one or more openings in the sensing tube 620) and an opposite end 658 of the same HCF 108 extends into the smaller segment 648 of the same sensing tube 620.

In order to measure the presence of gas leaking from the source 102, the gas typically enters the sensing tube 620 through one or more openings 122 (not shown in FIG. 5 but shown in FIG. 1) and gradually moves into the hollow core of one or more of the HCFs 108. The pump 124 may be fluidly coupled with the end 652 of the larger segment 646 of the sensing tube 620 to generate air flow along the flow direction 442. This air flow may move the leaking gas through the sensing tube 620, as described above.

The different cross-sectional areas 621, 623 of the segments 646, 648 of the sensing tube 620 can generate a pressure differential in the leaking gas across the opposite ends 656, 658 of one or more of the HCFs 108. The larger cross-sectional area 621 in the larger segment 646 of the sensing tube 620 causes the pressure of the leaking gas at the end 656 of one or more of the HCFs 108 to be higher than the pressure of the leaking gas at the end 658 of the same HCF(s) 108 in the smaller segment 648 (e.g., due to the smaller cross-sectional area 623). The gas and/or air flowing in the smaller segment 648 of the sensing tube 620 has a smaller cross-sectional area 623 in which to flow relative to the cross-sectional area 621 of the larger segment 646 of the sensing tube 620. As a result, the pressure differential is generated, with the pressure of the gas in the tube 620 being lower at, near, or closer to the end 658 of the HCF 108 than the opposite end 656 of the same HCF 108.

This pressure differential can cause the gas to be drawn, pulled, or otherwise sucked into the interior core of the HCF(s) 108. The pressure of gas leaking from the source 102 inside the sensing tube 620 may be lower in the smaller segment 648 than the larger segment 646. This lower pressure at the end 658 of the HCF 108 may cause the gas to be drawn, pulled, or sucked into the interior core of the HCF 108 through the end 656 of the HCF 108. Greater concentrations or amounts of the gas within an HCF 108 can result in the presence of the gas to be more likely to be detected than smaller concentrations within an HCF 108. As a result, the leaking gas may be detected sooner than in systems without the pressure differential.

Figure 6:
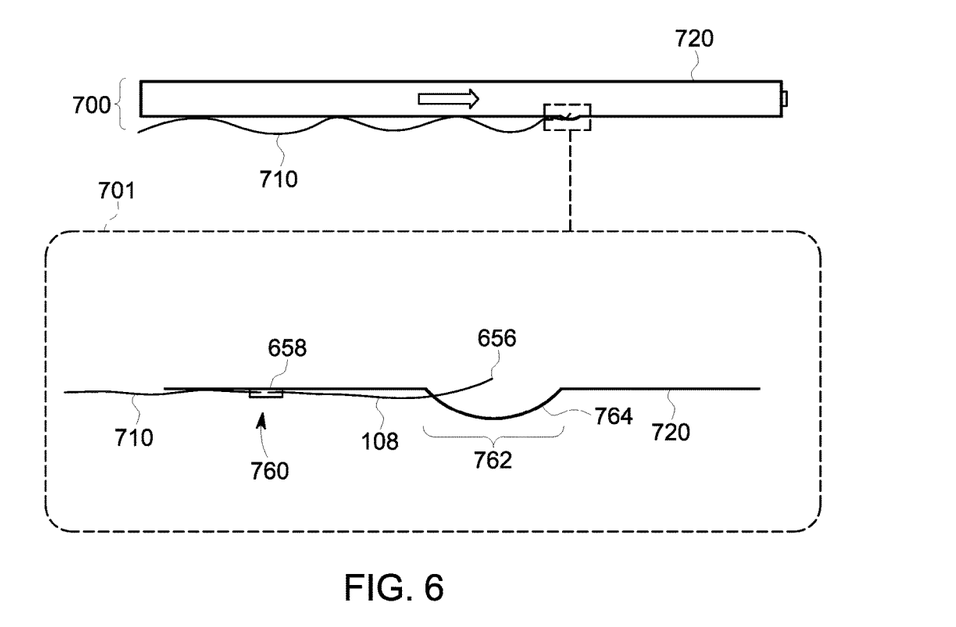
FIG. 6 illustrates a gas leak detection system according to another embodiment.

FIG. 6 illustrates a gas leak detection system 700 according to another embodiment. FIG. 6 also illustrates a magnified view 701 of a portion of the system 700. The system 700 includes a sensing tube 720, which may be similar or identical to the sensing tube 120 shown in FIG. 1. Although not shown in FIG. 6, the sensing tube 720 may include openings 122 (shown in FIG. 1) to allow gas leaking from the source 102 (shown in FIG. 1) to enter into the interior of the sensing tube 720.

One or more HCFs 108 are optically coupled with an interrogator 212 or 312 (not shown in FIG. 6, but shown in FIGS. 1 through 2) of the system 700 by one or more solid core fibers 710, which may be similar or identical to the solid core fibers 110, 210, or 310. In contrast to the gas leak detection systems and sensing tubes shown in FIGS. 1 through 4, the solid core fibers 710 and part or most (e.g., at least a majority) of the HCFs 108 are disposed outside of the sensing tube 720 in the system 700. The solid core fibers 710 may be attached to an exterior surface of the sensing tube 720, and may be connected with one or more HCFs 108 by a mechanical splice or connector 760. The splice 760 optically couples the solid core fiber 710 with the end 658 of the HCF 108 to permit light propagating through the solid core fiber 710 to enter into and propagate through the hollow core of the HCF 108. In one embodiment, the splice 760 may be used to optically couple the solid core fibers and HCFs of one or more other embodiments described herein. The splice 760 may be open to atmospheric pressure outside of the sensing tube 720.

A segment of the HCF 108 that includes the end 656 of the HCF 108 may be disposed inside the sensing tube 720 while a remainder of the HCF 108 is disposed outside of the sensing tube 720. In one embodiment, the segment of the HCF 108 that is inside the sensing tube 720 is shorter than the segment of the HCF 108 that is outside of the sensing tube 720. The sensing tube 720 includes one or more sensor openings 762 through which the HCF(s) 108 extend into the interior of the sensing tube 720. The sensor openings 762 may be openings in the sensor tube 720 in addition to the openings 122 through which gas leaking from the source 102 (shown in FIG. 1) enters into the sensing tube 720. Alternatively, one or more of the openings 122 through which the gas enters the sensing tube 720 may be used as one or more sensor openings 762.

The end 656 of the HCF 108 is inserted into the interior space of the sensing tube 720 through or via the sensor opening 762. A seal 764 is provided over the sensor opening 762 with the HCF 108 extending through the seal 764. The seal 764 may be a hermetic seal that does not allow gas or air inside the sensor tube 720 from flowing into or out of the sensor tube 720 through the sensor opening 762. The seal 764 may be formed from a rigid or elastic material, such as a thermoplastic material, a rubber material, etc.

As described above, gas leaking from the source 102 may enter into the interior of the sensing tube 720 through one or more openings 122 in the tube 720. This gas may enter into the hollow core of one or more HCFs 108 through the end(s) 656 of the respective HCFs 108. Light propagating outside of the sensing tube 720 in the solid core fiber(s) 710 may enter into the HCF 108 and optionally be reflected by a reflector at or near the end 656 of the HCF 108 to detect the presence of the gas in the hollow core of the HCF 108, as described above.

Placing the solid core fiber(s) 710 and at least a segment of the HCFs 108 outside of the sensing tube 720 allows for the system 700 to be added to an existing sensing tube 720 without having to replace or significantly alter the sensing tube 720. For example, while additional holes may need to be created in the sensing tube 720 to form the sensor openings 762, other alterations to the sensing tube 720 (including changes to the interior of the sensing tube 720) may not need to be made. This can allow for the embodiment of the system 700 shown in FIG. 6 to be used to easily retrofit an existing sensing tube with the system 700.

The end of tube 720 at which the flowing gas exits may additionally have a flow restriction or a relief valve. When air is pumped into tube 720 from the other end, the pressure inside tube 720 increases due to the restriction or relief valve. This generates a pressure differential across the HCF and causes gas within tube 720 to be forced into the opening 656 of the HCF because the other end of the HCF 658 is outside the tube and is at the lower atmospheric pressure.

Figure 7:
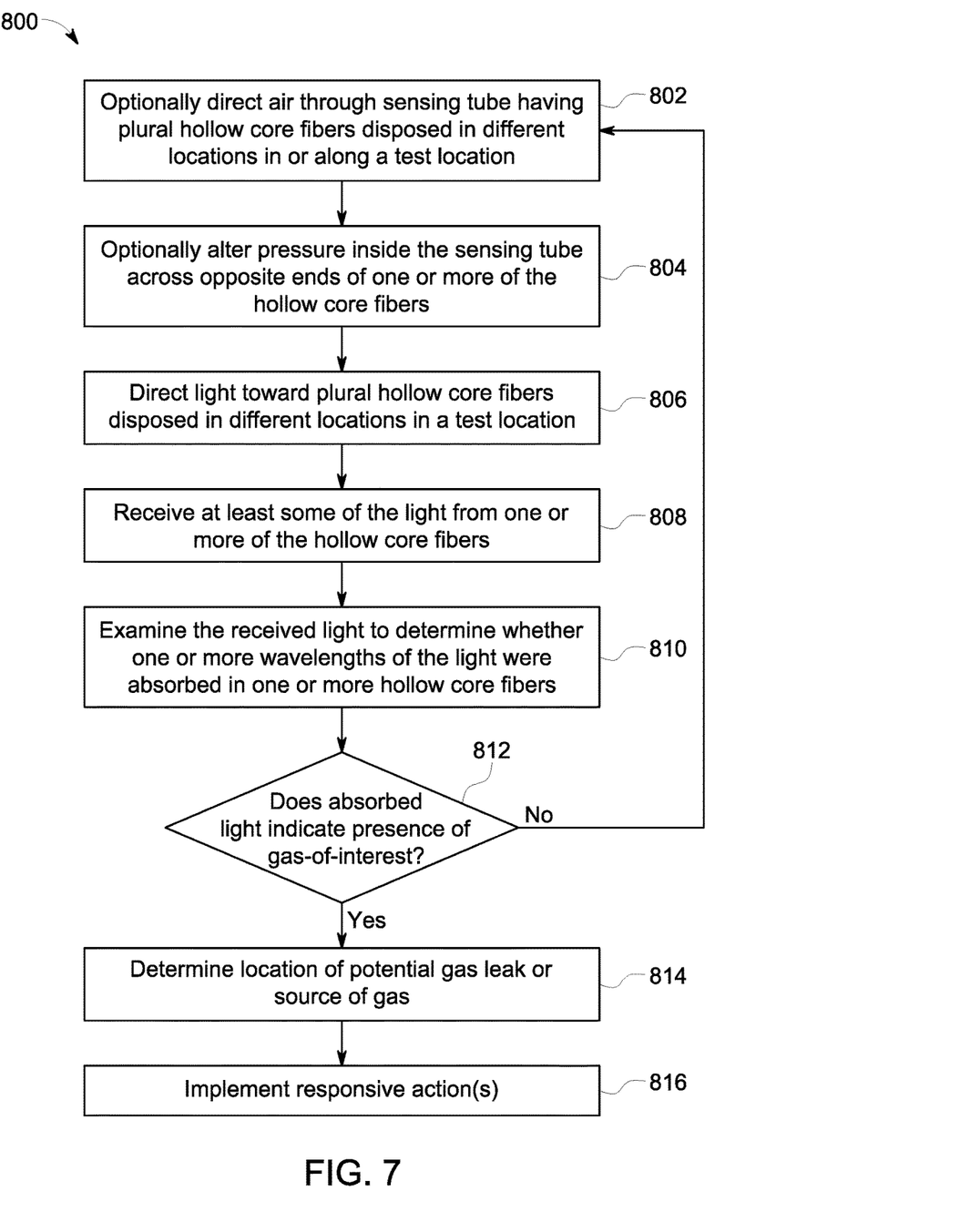
FIG. 7 illustrates a flowchart of one embodiment of a method for detecting presence of a gas-of-interest in a test location.

FIG. 7 illustrates a flowchart of one embodiment of a method 800 for detecting presence of a gas-of-interest in a test location. The method 800 may be performed by one or more embodiments of the systems described herein to detect the presence of a gas-of-interest, such as but not limited to methane, leaking from a pipeline, in an underground mine, on a mining platform, or in another location.

At 802, air is optionally directed through a sensing tube having plural hollow core fibers disposed in different locations in the sensing tube. This air may be pushed through the sensing tube to move the gas-of-interest through the sensing tube to aid in detection of the gas. The air may be forced through the sensing tube at periodic intervals, at selected or on-demand times, continuously, or at other times. For example, the air may not be continually forced or pumped through the sensing tube.

At 804, the pressure inside the sensing tube is optionally altered. The pressure may be altered to generate a pressure differential across or between opposite ends of one or more of the hollow core fibers, as described above. This pressure differential may be created in order to draw, pull, or suck air and/or gases in the sensing tube into the one or more HCFs to reduce the time period needed to detect the potential presence of a gas-of-interest. Alternatively, 804 may not be performed.

At 806, light is directed toward the plural hollow core fibers. The light may be directed toward the hollow core fibers with one or more designated or operator-selected wavelengths. These wavelengths may be selected based on the gas-of-interest. For example, different gases may absorb different amounts of different wavelengths of light. Controlling the wavelength(s) of light propagating to and into the hollow core fibers allows for determination of which gas(es) are detected. The light may be directed to the hollow core fibers through one or more solid core fibers, as described above.

At 808, at least some of the light is received after passing through one or more of the hollow core fibers. For example, the light may pass through the hollow core fibers and a portion of the light may be absorbed by gas(es) in one or more of the hollow core fibers. Optionally, the light may pass through one or more hollow core fibers and be reflected back by reflectors in or connected with the hollow core fibers.

At 810, the light that is received is examined to determine whether one or more wavelengths of the light were absorbed in one or more of the hollow core fibers. A reduction in amplitude of one or more wavelengths of the light (e.g., in terms of numbers of photons detected, intensity, or other measurement) relative to other wavelengths of light may indicate that the reduced wavelength or wavelengths of light were absorbed by a gas within one or more of the hollow core fibers.

At 812, a determination is made as to whether the absorbed light indicates the presence of a gas-of-interest. For example, if one or more wavelengths of the light were reduced, then a determination may be made as to whether the wavelength or wavelengths that were reduced are the wavelengths of light absorbed by the gas-of-interest. If the gas-of-interest does not absorb these wavelengths of light, then the gas-of-interest may not be present at the hollow core fiber (from which the light being examined was received). As a result, flow of the method 800 can return toward 802 or optionally, toward 804, toward 806, or may terminate. But, if the gas-of-interest does absorb these wavelengths of light, then the gas-of-interest may be present at the hollow core fiber (from which the light being examined was received). As a result, flow of the method 800 can proceed toward 814.

At 814, a location of the gas-of-interest is determined. For example, based on the location of the hollow core fiber that reduced the one or more wavelengths of light that are absorbed by the gas-of-interest and the rate of flow of the air through the sensing tube, the location of a leak of the gas or a source of the gas can be determined. The location may be determined by calculating the time for the air to flow to the hollow core fiber before the gas signal is detected, and by calculating the distance from the source of the gas based on this time.

At 816, one or more responsive actions may be implemented. For example, responsive to detecting a gas leak or source of gas, the processors 118 may generate and communicate an alarm signal that causes an output device (e.g., a light, a speaker, etc.) to warn of the presence of the gas and the location of the gas. Optionally, the alarm signal may be communicated to a pump that is moving the gas through a pipeline to shut off the pump and stop moving the gas through the pipeline. Alternatively, one or more other actions may be implemented.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

It should be noted that the various embodiments may be implemented in hardware, software or a combination thereof. The various embodiments and/or components, for example, the modules, or components and controllers therein, also may be implemented as part of one or more computers or processors. The computers or processors may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A system comprising:
   one or more hollow core fibers disposed in different locations;

one or more solid core fibers optically coupled with the one or more hollow core fibers and configured to receive light of one or more wavelengths from a light source; and an interrogator device configured to receive at least some of the light propagating through the one or more solid core fibers and the one or more hollow core fibers, the interrogator device configured to identify a location of a presence of a gas-of-interest by examining absorption of at least one of the wavelengths of the light in at least one of the hollow core fibers;

wherein the one or more hollow core fibers are disposed at different distances along a length of an elongated sensing tube.

2. The system of claim 1, wherein the system includes plural hollow core fibers and plural solid core fibers, with each of the hollow core fibers connected to a single and different solid core fiber.

3. The system of claim 1, wherein the one or more hollow core fibers and the one or more solid core fibers are disposed at least partially within the elongated sensing tube having openings through which the gas-of-interest may enter into the sensing tube from a source of the gas-of-interest.

4. The system of claim 3, wherein the sensing tube includes an interior surface having one or more reduced throats with a smaller cross-sectional area at a first end of one or more of the hollow core fibers than a cross-sectional area of the interior surface at an opposite, second end of the one or more hollow core fibers.

5. The system of claim 3, wherein one or more of the hollow core fibers are coupled with a baffle outwardly extending from the hollow core fiber, the baffle located closer to a first end of the hollow core fiber than an opposite, second end of the hollow core fiber, wherein the baffle reduces a cross-sectional area of the sensing tube at the first end of the hollow core fiber relative to the second end of the hollow core fiber.

6. The system of claim 3, wherein the sensing tube includes a larger segment fluidly coupled with a smaller segment, the larger segment having a larger cross-sectional area than the smaller segment, wherein a first end of one or more of the hollow core fibers is disposed in the larger segment of the sensing tube and an opposite, second end of the one or more hollow core fibers is disposed in the smaller segment of the sensing tube.

7. The system of claim 1, wherein the one or more solid core fibers are disposed outside of an elongated sensing tube having openings through which the gas-of-interest may enter into the sensing tube from a source of the gas-of-interest, and wherein the one or more hollow core fibers include first ends extending into an interior space of the sensing tube and opposite, second ends optically coupled with the solid core fibers outside of the sensing tube.

8. The system of claim 7, wherein a second solid core fiber is attached to the end of at least one of the hollow core fibers which extends into an interior space of the sensing tube.

9. The system of claim 1, wherein the one or more solid core fibers are disposed outside of an elongated sensing tube having openings through which the gas-of-interest may enter into the sensing tube from a source of the gas-of-interest, and wherein the one or more hollow core fibers include first ends extending into an interior space of the sensing tube and optically coupled with the solid core fibers outside of the sensing tube, and second ends that are outside of the elongated sensing tube.

10. The system of claim 9, wherein a second solid core fiber is attached to the end of the hollow core fiber located outside of the sensing tube.

11. The system of claim 1, wherein the one or more hollow core fibers are configured to be disposed at the different locations in one or more of an underground mine, a mining platform, or a sensing tube extending along a pipeline.

12. A system comprising:
one or more hollow core fibers disposed in different locations;

one or more solid core fibers optically coupled with the one or more hollow core fibers and configured to receive light of one or more wavelengths from a light source;

an elongated sensing tube having openings through which a gas-of-interest may enter into the sensing tube from a source of the gas-of-interest, wherein the one or more hollow core fibers are at least partially disposed inside the sensing tube; and an interrogator device configured to receive at least some of the light propagating through one or more of the solid core fibers and one or more of the hollow core fibers, the interrogator device configured to identify a location of a presence of the gas-of-interest from the source by examining absorption of at least one of the wavelengths of the light at one or more of the hollow core fibers;

wherein the one or more hollow core fibers and the one or more solid core fibers are disposed within the sensing tube.

13. The system of claim 12, wherein the one or more hollow core fibers are disposed at different distances along a length of the sensing tube.

14. The system of claim 12, wherein the sensing tube includes an interior surface having one or more reduced throats with a smaller cross-sectional area at a first end of one or more of the hollow core fibers than a cross-sectional area of the interior surface at an opposite, second end of the one or more hollow core fibers.

15. The system of claim 12, wherein one or more of the hollow core fibers are coupled with a baffle outwardly extending from the hollow core fiber, the baffle located closer to a first end of the hollow core fiber than an opposite, second end of the hollow core fiber, wherein the baffle reduces a cross-sectional area of the sensing tube at the first end of the hollow core fiber relative to the second end of the hollow core fiber.

16. The system of claim 12, wherein the sensing tube includes a larger segment fluidly coupled with a smaller segment, the larger segment having a larger cross-sectional area than the smaller segment, wherein a first end of one or more of the hollow core fibers is disposed in the larger segment of the sensing tube and an opposite, second end of the one or more hollow core fibers is disposed in the smaller segment of the sensing tube.

17. The system of claim 12, wherein the one or more solid core fibers are disposed outside of an elongated sensing tube having openings through which the gas-of-interest may enter into the sensing tube from a source of the gas-of-interest, and wherein the one or more hollow core fibers include first ends extending into an interior space of the sensing tube and opposite, second ends optically coupled with the one or more solid core fibers outside of the sensing tube.

18. The system of claim 12, wherein the one or more solid core fibers are disposed outside of an elongated sensing tube having openings through which the gas-of-interest may enter into the sensing tube from a source of the gas-of-interest, and wherein the one or more hollow core fibers include first ends extending into an interior space of the sensing tube which are optically coupled with the one or more solid core fibers outside of the sensing tube and opposite, second ends optically coupled with the one or more solid core fibers outside of the sensing tube.

19. A method comprising:
- receiving light that has propagated through one or more solid core fibers and one or more hollow core fibers of several hollow core fibers disposed in different locations;
- determining whether one or more wavelengths of the light have been at least partially absorbed by a gas-of-interest inside one or more of the hollow core fibers based on the light that is received;
- determining a location of a source of the gas-of-interest based on a location of the one or more hollow core fibers in which the one or more wavelengths of the light was at least partially absorbed by the gas-of-interest; and
- drawing the gas-of-interest into the one or more hollow core fibers by generating a pressure differential of the gas-of-interest between opposite ends of the one or more hollow core fibers.

20. The method of claim 19, further comprising stopping a flow of the gas-of-interest in a pipeline responsive to determining the location of the source of the gas-of-interest.

* * * * *